(12) United States Patent (10) Patent No.: US 8,728,537 B2
Wannowius et al. (45) Date of Patent: *May 20, 2014

(54) COMPOSITIONS FOR IMPROVEMENT OF WOUND HEALING

(71) Applicant: Cytotools AG, Darmstadt (DE)

(72) Inventors: Klaus J. Wannowius, Ober-Ramstadt (DE); Dirk Kaiser, Eppertshausen (DE)

(73) Assignee: Cytotools AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,325

(22) Filed: Dec. 28, 2012

(65) Prior Publication Data

US 2013/0129837 A1 May 23, 2013

Related U.S. Application Data

(63) Continuation of application No. 12/574,849, filed on Oct. 7, 2009, now Pat. No. 8,349,369, which is a continuation of application No. 10/580,392, filed as application No. PCT/EP2004/013212 on Nov. 22, 2004, now Pat. No. 7,618,655.

(30) Foreign Application Priority Data

Nov. 21, 2003 (DE) .................................. 103 54 768

(51) Int. Cl.
*A61K 33/14* (2006.01)
*A01N 59/08* (2006.01)

(52) U.S. Cl.
USPC ............................ 424/661; 424/400; 424/401

(58) Field of Classification Search
USPC .......................................... 424/400, 401, 661
See application file for complete search history.

(56) References Cited

U.S. PATENT DOCUMENTS

| | | | |
|---|---|---|---|
| 2,701,781 A | 2/1955 | de Guevara | |
| 3,123,521 A | 3/1964 | Wentworth | |
| 3,147,124 A | 9/1964 | Wentworth | |
| 4,084,747 A | 4/1978 | Alliger | |
| 4,296,103 A | 10/1981 | Laso | |
| 4,507,285 A | 3/1985 | Kuhne | |
| 4,838,934 A | 6/1989 | Elsenheimer et al. | |
| 5,695,752 A | 12/1997 | Rosen et al. | |
| 6,103,950 A | 8/2000 | Rimpler et al. | |
| 6,171,485 B1 | 1/2001 | Kuke | |
| 2003/0133878 A1 | 7/2003 | Hinze | |

FOREIGN PATENT DOCUMENTS

| | | |
|---|---|---|
| DE | 44 05 800 C1 | 7/1995 |
| DE | 195 18 464 A1 | 11/1996 |
| DE | 199 50 632 A1 | 5/2001 |
| EP | 0093875 A1 | 11/1983 |
| EP | 0 255 154 A1 | 2/1988 |
| WO | WO-84/03274 A1 | 8/1984 |
| WO | WO-89/05343 A1 | 6/1989 |
| WO | WO-96/18300 A2 | 6/1996 |
| WO | WO-96/33947 A1 | 10/1996 |
| WO | WO-97/06098 A1 | 2/1997 |
| WO | WO-00/48940 A1 | 8/2000 |
| WO | WO-01/12205 A2 | 2/2001 |
| WO | WO-03/050044 A1 | 6/2003 |

OTHER PUBLICATIONS

Translation for WO/00/48940 Aug. 24, 2000.*
Data and Instructions for the Use of Immunokine® WF10 (TCDO) I.V. Solution for Intravenous Infusion with declaration signed by Dr. Rainer Martin and dated Sep. 6, 2010, filed by the opponent in opposition proceedings of European Patent No. EP1687238 (2 pp.).
Research Statement by Gilbert Gordon, dated Sep. 3, 2010, filed by the opponent in opposition proceedings of European Patent No. EP1687238 (52 pp.).
Test report—enclosure to the opposition of Nuvo Manufacturing GmbH dated Sep. 7, 2010, filed by the opponent in opposition proceedings of European Patent No. EP1687238 (17 pp.).
Reply of the patent proprietor to the notice of opposition in EP1687238, dated Apr. 15, 2011 (13 pp.).
Brief from ChemCon GmbH to Dr. Kaiser regarding EP 1687238 (Jan. 21, 2011), filed by the patent proprietor in opposition proceedings of European Patent No. EP1687238 (1 page).
Lücker, Gutachtlich-Facharztliche Stellungnahme zur Wirksamkeit des Therapeutikums DermaPro (DPOCL—Losung) (2011).
Jaenicke (ed.), Dynamics and Chemistry of Hydrometeors: Final Report of the Collaborative Research Centre 233 "Dynamik und Chemie der Hydrometeore", Collaborative Research Centres, Wiley-VCH, pp. 478-479.
Peracetic acid, source: http://en.wikipedia.org/w/index.php?oldid==415311016 (5 pp.).
Acetic Acid, Source: http://en.wikipedia.org/w/index.php?oldid-419118285 (13 pp.).
Jaenicke (ed.), Dynamics and Chemistry of Hydrometeors: Final Report of the Collaborative Research Centre 233 "Dynamik und Chemie der Hydrometeore", Wiley-VCH, pp. 471-472.
Francisco, Ab Initio Characterization of HOClO3 and HO4Cl: Implications for Atmospheric Chemistry, J. Phys. Chem., 99:13422-5 (1995).
Summons to attend oral proceeding in opposition proceedings of European application No. EP04798031.3, dated Jun. 29, 2011 (5 pp.).
Response to summons for oral proceedings dated Apr. 4, 2012, filed by the opponent in opposition proceedings of European Patent No. EP1687238.
Dr. Rainer Martin, Curriculum Vitae, dated Mar. 12, 2012, filed by the opponent in opposition proceedings of European Patent No. EP1687238.

(Continued)

*Primary Examiner* — Abigail Fisher
*Assistant Examiner* — Luke Karpinski
(74) *Attorney, Agent, or Firm* — Marshall, Gerstein & Borun LLP

(57) ABSTRACT

This invention relates to aqueous solutions of reactive chlorine compounds having the empirical formulae $H_2Cl_2O_6$ or $ClO_3H$, for example, and the derivatives, anions or salts thereof. The invention further relates to methods for the production of said compounds and the use thereof in the pharmaceutical and particularly in the medical field, in cosmetics, medicinal care and in the domains of food technology and technology.

15 Claims, 8 Drawing Sheets

(56) References Cited

OTHER PUBLICATIONS

Additional Declaration of Professor Gilbert Gordon, dated Mar. 16, 2012, filed by the opponent in opposition proceedings of European Patent No. EP1687238.
Letter (with English translation) dated Apr. 11, 2013, from patent proprietor to the European Patent Office regarding the submission of grounds of opposition dated Oct. 10, 2012, and the decision concerning this dated Oct. 17, 2012, in opposition proceedings of European Patent No. 1687238.
Response from opponent filed on Jun. 18, 2013, with the European Patent Office in response to the counterarguments dated Apr. 11, 2013, in opposition proceedings of European Patent No. 1687238.
Reply (with English translation) filed by patent proprietor, dated Sep. 30, 2013, with the European Patent Office in response to the submission of the opponent dated Jun. 18, 2013, in opposition proceedings of European Patent No. 1687238.
Bogdanchikov et al.,"The Mechanism of the Elementary Act of HO2—Anion Oxidation by the ClO2 Radical in Aqueous Solution," *J. Chem. Phys.*, 2(5):1041-1054 (1985).
Bowers, "Stimulation of Lymphocytes with Periodate or Neuraminidase Plus Galactose Oxidase," *Methods in Enzymology*, 150:105-109 (1987).
Davidson et al., "An Investigation of Photochemically Induced Reactions in a Chlorine-Ozone System at -10.5 and 0.0 Degrees," *J. Phys. Chem.*, 77(21):2515-2520 (1973).
Fenwick, "The Treatment of Cancer by the use of Potassium Biohromate," *British Medical Journal*, pp. 589-590 (1909).
Granstrom et al., "Generation and Use of Chlorine Dioxide in Water Treatment," *Journal of the American Water Works Assoc.*, pp. 1453-1466 (1958).
Los et al., "Hydrogen Peroxide as a Potent Activator of T Lymphocyte Functions," *Eur. J. Immunol.*, 25:159-165 (1995).
Matzinger, "Tolerance, Danger, and the Extended Family," *Annu. Rev. Immunol.*, 12:991-1045 (1994).
Schreck et al., "Reactive Oxygen Intermediates as Apparently Widely Used Messengers in the Activation of the NF-$_\chi$B Transcription Factor and HIV-1," *EMBO Journal*, 10(8):2247-2258 (1991).
Stenzel et al., "Mitogenic and Co-Mitogenic Properties of Hemin," *J. Immun.*, 127(6):2469-2473 (1981).
Svensson, "Infrared Spectroscopic and Ab Initio Study of HOOClO2," *J. Phys. Chem. A.*, 103:4432-4437 (1999).
Wang et al., "Adoptive Immunotherapy for Stage IV Renal Cell Carcinoma: A Novel Protocol Utilizing Periodate and Interleukin-2-Activated Autologous Leukocytes and Continuous Infusions of Low-Dose Interleukin-2," *The American Journal of Medicine*, 83:1016-1023 (1987).

International Search Report for Application No. PCT/EP2004/013212, dated Mar. 15, 2005.
International Preliminary Report on Patentability for Application No. PCT/EP2004/013212, dated Jan. 23, 2007.
Notice of Opposition in European Patent No. EP1687238, dated Sep. 7, 2010 (4 pp.).
Reasons for the Opposition dated Sep. 7, 2010, filed by the opponent in opposition proceedings of European Patent No. EP1687238 (14 pp.).
Response made by Dr. Jurgen Schultheiss dated Apr. 30, 2012, filed by the patent proprietor in opposition proceedings of European patent No. 1687238.
EU Clinical Trials Register, EudraPCT No. 2010-020437-12, a multicentric, double blind, comparative Phase II b study of the efficacy of a wound healing solution in patients with diabetic foot ulcer (6 pages) (Apr. 17, 2012).
Oktettregel, Wikipedia (German) entry and English translation "Octet Rule" from Wikipedia English (2012).
EU Clinical Trials Register, EudraCT No. 2007-007748-85, DermaPro in Wounds with Impaired Healing (Phase II) (Apr. 17, 2012).
Chlorate, Wikipedia (English) entry (3 pp.) (2012).
Response made by Dr. Jutta Wagner dated May 4, 2012, filed by the opponent in opposition proceedings of European patent No. 1687238.
Chlorate, Wikipedia (German) entry (2 pp.) (May 3, 2012).
Yingsakmongkol et al., Effect of WF10 (immunokine) on diabetic foot ulcer therapy: a double-blind, randomized, placebo-controlled trial, J. Foot & Ankle Surgery (6 pp.) (2011).
Hinz et al., Rationale for and results from a randomised, double-blind trial of tetrachlorodecaoxygen anion complex in wound healing, The Lancet (Apr. 12, 1986).
Raffanti et al., Randomized, double-blind, placebo-controlled trial of the immune modulator WF10 in patients with advanced aids, Infection, 26(4): 6pp. (2008).
European Patent Office, Information Notice in opposition proceedings of European application No. 04798031.3, dated May 8, 2012.
European Patent Office, Minutes of Oral Proceedings, Decision of the Opposition Division, and Grounds for the Decision in opposition proceedings of European Application No. 04798031.3, dated Jun. 6, 2012.
Ashcroft, An Introduction to Mass Spectrometry, retrieved from the Internet at <http:www.astbury.leeds.ac.uk/facil/MStut/mstutorial.htm> on Jan. 31, 2013.
Statement of Grounds for the Appeal dated Oct. 10, 2012, filed by the appellant/opponent in appeal proceedings of European Patent No. 1687238.

\* cited by examiner

COMPOSITIONS FOR IMPROVEMENT OF WOUND HEALING

CROSS-REFERENCE TO RELATED APPLICATIONS

This is a continuation of U.S. Ser. No. 12/574,849 filed Oct. 7, 2009, which is a continuation of U.S. Ser. No. 10/580,392, which is the U.S. national phase of PCT/EP2004/013212 filed Nov. 22, 2004, which in turn claims the priority of DE 103 54 768.1 filed Nov. 21, 2003, the entire respective disclosures of which are incorporated herein by reference.

BACKGROUND OF THE INVENTION

1. Field of the Invention

The invention relates to reactive chlorine compounds such as dichloric acids, the intermediate product peroxochloric acid as well as peroxochlorous acid and their individual derivatives, anions, and/or salts. It further relates to processes for manufacturing these compounds and their use in the pharmaceutical field, here in particular, in medical treatment as drugs and disinfectants, in the fields of cosmetics and medicinal care as histocompatible deodorants, in the field of foodstuff treatment and technology, in particular in the preservation of foods and beverages, as a bleaching agent and for drinking water disinfection, in the antimicrobial treatment of plants and fruits in agriculture, and as an oxidizing agent in technical chemistry and for cleaning waste gas.

2. Related Technology

Oxidizing agents have a very wide range of applications in technical chemistry, in hygiene and in food preservation, in cosmetics and also in pharmaceutical uses.

According to Polly Matzinger (Polly Matzinger: "Tolerance, Danger, and the Extended Family" in Annu. Rev. Immunol. 1994, 12) cells dying due to violence, i.e. through massive radiation effects, toxic substances, parasitic, bacterial or viral infective agents, lytic, non-apoptotic effects, emit danger signals. These must persist so that the body's own defences, which as well as the actual antigen signal require a non-specific co-stimulation from antigen-presenting cells (e.g. macrophages), can have an optimum clinical effect.

During a violent, non-apoptotic cell death, phagocytes (so-called micro and macrophages) are responsible for cellular debris disposal. In this debris disposal process oxidatively effective oxygen metabolites are released. Hydrogen peroxide ($H_2O_2$) is the most well-known of these substances. In-vitro-trials show that, in the micromolar range, $H_2O_2$ can lead to an immune modulation of lymphocytes via the activation of the transcription factor HF-kappa B (R. Schreck et al., The EMBO Journal 10(8), 2247-58 (1991); M. Los et al., Eur. J. Immunol. 25, 159-65 (1995). The working group of Avraham Novogrodsky was the first to demonstrate in vitro that certain oxidizing agents (Bowers W. E.: "Stimulation of Lymphocytes with Periodate or Neuraminidase plus Galactose Oxidase—NAGO" p. 105-109, Review in Immunochemical Techniques Part K Methods in Enzymology Vol. 150, 1987), among other effects, also increase the $H_2O_2$ formed in the body itself co-mitogenically by lymphocyte proliferation due to antigen stimulation, if macrophages are simultaneously present in the lymphocyte culture (Stenzel K. H., Rubin A. L., Novogrodsky A.: "Mitogenic and Comitogenic Properties of Hemin." J. Immunol. 127, 6: 2469-2473 et ibid. cit. ref.). An immune response will be incomplete or not even take place at all if the oxidatively effective oxygen metabolites are not formed in sufficient quantities in the body. Thus a tolerance or pathological anergy results. If the metabolites are produced excessively or for a disproportionately long period, then chronic inflammation and tissue scars will form.

As a result of these findings, one can assume that oxidatively effective oxygen compounds will have a therapeutic effect, particularly in such clinical situations where their endogenous formation is insufficient or deteriorates before the body injuries have completely healed and the infective agents have been totally removed. A treatment success is expected especially in those cases where the cells are indeed affected by the infection but not destroyed and therefore do not emit "danger signals". Exemplary here are infections with leprosy and tuberculosis bacilli as well as infections caused by herpes and AIDS (HIV) viruses.

A report was published as early as 1906 on the successful clinical use of potassium bichromate in the healing of ichorous chronic wounds (Fenwick, J.: "*The Treatment of Cancer by the Use of Potassium Bichromate*", British Medical Journal, Mar. 6, 1909, 589-591).

Further numerous publications, which have appeared in the meantime, show that hydrogen peroxide formed physiologically within the body—as well as the in vivo even more short-lived peroxonitrite which can also form from the equally physiological nitroxide and hydrogen peroxide—also demonstrates wound healing effects, whereby a positive immunomodulation plays an essential role. For example, the EPA-0390829 describes a method for increasing the syngenic intradermal cell proliferation through human growth factors using hydrogen peroxide injections. Such a comitogenic increase in the growth factor effects of interleukin-2 was also described for periodate in 1987 (Wang J. et al., The American Journal of Medicine 1987, 83: 1016-1023).

It is known that (co)mitogenic oxidants have intolerable side effects, such as e.g. for bichromate:—the now recognized carcinogenic effect of chromium oxide: For periodate:—iodine hypersensitivity and toxic effects. Therefore, their clinical use has to take place laboriously as an "adoptive transfer", i.e. the blood cells are taken out, treated in vitro and then returned in vivo—as described in the previously quoted study by J. Wang et al. 1987. For NAGO side effects are:—the foreign protein sensitization: For $H_2O_2$:—the formation of toxic oxygen radicals. Here too, there are also technical problems concerning their use as drugs, e.g. for $H_2O_2$:—short storage life in diluted aqueous solution; the catalase lability with massive oxygen gas release. For oxidized ubichinon derivatives problems are:—pharmaceutical manufacturing problems and limited bioavailability.

Therefore, it was not possible up to now to transfer the experimentally demonstrated immunopharmacological action of (co)mitogenic oxidants in clinical practice into tissue regeneration/wound healing, infection resistance and the strengthening of the immune response. In clinical practice, as well as a local application, a systemic treatment, usually in the form of an intravenous administration, is also desirable.

Theo Gilbert Hinze (US 2003/0133878 A1, "American Composition for the treatment of legionella pneumophila and a method for such treatment") processed aqueous solutions of NaCl or $KCl_2$ (presumably the latter chemical formula here is a printing error) with electrochemical oxidation at pH 6.5-7.5. It was conjectured that, as well as other ions, only the $Cl_2O_6^{2-}$ ion could be present which at that time had been described only in the preceding invention. This dimer contains the chlorine atoms in the +3 and +5 valence states.

The patent literature contains descriptions of a few further chlorine-oxygen preparations which are particularly used in such technical fields where they serve as oxidants not only in industrial technology as bleaching agents and deodorants, but also where they are recommended for paramedical applications such as in cosmetics for skin and hair care, for household cleaning, in the sanitary sector for hygiene and/or as disinfectants for surfaces (U.S. Pat. Nos. 2,701,781; 3,123,521) and/or wounds (U.S. Pat. No. 4,084,747; EP-A-0 744 895), as preservation agents for cheese (U.S. Pat. No. 3,147,124) and for the conditioning of drinking and bathing water (U.S. Pat. No. 4,296,103; DE-A-44 05 800, DE-A-19 518 464; WO 96/33947; WO 97/06098). The U.S. Pat. No. 4,296,103, EP-A-0 136 309, U.S. Pat. No. 4,507,285 and EP-A-0255145 describe the medical application of chlorine-oxygen preparations.

WO 00/48940 contains a description of the preparation of a chlorohydroperoxide with the formula $HOOClO_2$ where the chlorine has valence of 5. This hydroperoxide behaves as an acid which supplies the anion $O_2ClOO^-$ in an aqueous environment. Therefore, it was called peroxochloric acid and its anion is called peroxochlorate. It is reported that the combination of two peroxochlorate ions, under separation of an oxygen molecule, can lead to derivatives of peroxochlorate with one peroxo group and two chlorine atoms with different valences. This ion is allocated the empirical formula $(Cl_2O_6)^{2-}$.

It is disclosed that it would be possible to manufacture stable peroxochloric acid and stable salts or anions thereof in solution. For example, these compounds are obtained in aqueous solution by the reaction of chlorine dioxide with hydrogen peroxide if the work is carried out at pH values which are equal to, or greater than, the pKs value of peroxochloric acid ($HOOClO_2$). pH values of 6.5 and more are preferable, and the pH range of 10-12 is especially preferable.

Thus, in WO 00/48940 peroxochloric acid or its salts, peroxochloric acid and its salts or anions in aqueous solution, oligomeric derivatives of the peroxochlorate with mixed-valent chlorine atoms and their salts or anions in aqueous solution as well as the carbon dioxide adduct as an acid, an anion in solution or as a salt are disclosed.

In the meantime, it has been proved that an isolation of a crystalline metallic salt of peroxochlorate, according to the specifications given in WO 00/48940, is unsuccessful.

Due to the low concentrations of peroxochlorate in the preparations manufactured according to the specifications of WO 00/48940, it is only possible to prepare the deoxo dimers to a limited degree.

Svensson and Nelander published the preparation of $HOOClO_2$ at low temperatures of 17K (−256, 15° C.) in J. Phys. Chem. A 1999, 103, 4432-4437.

Therefore, all the published chlorine-oxygen preparations do not fulfil the requirement criteria of modern drug approval. These state that the pharmacodynamics of the preparation must be allocatable to a chemically defined compound as the so-called active substance which is to be standardized as the pharmaceutical product. This is also necessary in order to guarantee homogeneous drug quality.

The intrinsically good chlorine-oxygen compounds of WO 00/48940, and in particular the deoxo dimer defined there, can, up to now, only be manufactured to a limited degree. Therefore, a commercial exploitation appears to be impossible.

GENERAL DESCRIPTION OF THE INVENTION

The invention provides an oxidant without the disadvantages described above. As well as the usual technical, medicinal and disinfectant fields of application, such an oxidant should also offer the possibility of formulation as a medicament for both local and systemic treatment, e.g. for intravenous application as, for example, a drug for tissue regeneration, for wound healing and against infections or for enhancing the immune response. Furthermore, it should fulfill the requirements of modern new drug approval procedures.

Particularly, therefore, the invention provides a further improved oxidant and an improved process for its manufacture and application.

Surprisingly, it has become evident that this object can be solved through the preparation of reactive chlorine compounds such as dichloric acids, the intermediate product peroxochloric acid as well as peroxochlorous acid, as well as their individual derivatives, anions and/or salts.

The novel dichloric acids, according to the invention, are shown in the following Table 1. Among these dichloric acids, the acids numbered No 1 to No. 3 are particularly preferred embodiments of this invention.

TABLE 1

| No. | Formal oxidation numbers of chlorine | Structural formula of the acid | Structural formula of the dianion |
|---|---|---|---|
| 1 | +5, +5 | $O=Cl(-O-)-O-Cl(=O)(-O_H)-O-H$ | $O=Cl(-O-)-O-Cl(=O)(-O^-)-O^-$ |
| 2 | +6, +4 | $O=Cl(=O)-Cl(-O-H)(-O-H)$ with double bonds | $O=Cl(=O)-Cl(-O^-)(-O^-)$ |
| 3 | +5, +5 | $H-O-Cl(=O)(=O)=Cl(=O)(=O)-O-H$ | $O^--Cl(=O)(=O)=Cl(=O)(=O)-O^-$ |

TABLE 1-continued

| No. | Formal oxidation numbers of chlorine | Structural formula of the acid | Structural formula of the dianion |
|-----|---|---|---|
| 4 | +5, +3 | O=Cl(=O)—O—O—Cl(O—H)—O—H | O=Cl(=O)—O—O—Cl(O⁻)(O⁻) |

As well as the valence pairs already described previously +3/+5 (WO 00/48940) and +4/+4 (Bogdanchikov et al.), the dichloric acids according to the invention No. 1 to No. 3 with valences of +6/+4 and +5/+5 for chlorine were manufactured for the first time according to the process of the invention. The anion of the acid of No. 4 is described in WO 00/48940. The manufacturing process described there, however, does not work.

In WO 00/48940 the postulation was made that the deoxo dimer is formed from two molecules of a reactive chlorine-oxygen species (peroxochlorate) via the reaction

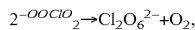

whereby the chlorine atoms are present in the oxidation numbers +3 and +5. However, the manufacture of a stable compound according to example 6 of WO 00/48940, which is desirable under pharmaceutical law aspects, is not successful.

The formation of the dimeric derivative from 2 molecules of peroxochlorate according to the formula

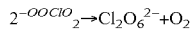

can namely only be expected at very high concentrations of peroxochlorate (roughly from 2 to 3 mol/L). Such high concentrations, however, are impossible in practice due to the high instability of the compound.

However, the examinations which led to the invention show that the reaction of peroxochlorate ions $O_2ClOO^-$ with chlorite ions ($ClO_2^-$) leads surprisingly directly to the palette of "dimeric" $Cl_2O_6^{2-}$ species:

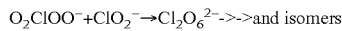

Furthermore, surprisingly, with the help of the process according to the invention, the preparation of the previously unknown peroxochlorite ion, O=ClOO⁻ and the peroxochlorous acid O=ClOOH derived from it is successful—in particular in the solutions containing chlorite according to the invention.

These chlorine compounds have not been described previously.

Especially round about the point of neutrality, the dissociation of the dichlorine species $Cl_2O_6^{2-}$ into chlorate ions $ClO_3$ and peroxochlorite ions OClOO⁻ is a clearly competitative reaction to the described intramolecular redox reactions of the dichlorine species which lead to the compounds 1-4 in the above table.

Insofar as reference is made to anions in the disclosure, the presence of the necessary counterions (particularly in solution) is included as well. The term "anions" is used in particular to stress that, in solution, the dichlorate is the more stable form compared with the protonated acid. However, the term "anion" can, according to the invention, and depending on the context, also be used in place of acid. The term "acid" can equally be used in place of "anion".

The invention also relates to the process of manufacturing preparations which contain the dichloric acids and their derivatives, anions and/or salts, and/or the peroxochlorous acid according to the invention and its derivatives, anions and/or salts.

If one carries out the following steps, one can, in an amazingly simple way, manufacture the dichloric acids and the peroxochlorite ion according to the present invention.

Chlorine dioxide reacts with an aqueous solution or water-containing solution of hydrogen peroxide or another hydroperoxide or peroxide at a pH value of ≥6.5, the pH value is lowered by adding an acid, the gaseous free reactive chlorine compound, preferably the protonated peroxochlorine compound, is expelled with a cooled gas and collected in an alkaline solution, the collected free reactive chlorine compound, preferably the peroxochlorine compound, is incubated at a pH between 6 and 8, preferably about 7 with an up to 100-fold excess, preferably up to a 10-fold chlorite excess.

The dichloric and peroxochlorous acids of the invention, and also the ions which are present at physiological pH values can therefore, according to the invention, also be present as a mixture with peroxochlorate and chlorite in solution. Such a solution containing dichloric acids, peroxochlorous acid, peroxochlorate and chlorite according to the invention, therefore counts among the particularly preferable experimental practice examples of the invention.

In WO 00/48940, in contrast, chlorite-free solutions were produced in which the dichloric acids and the peroxochlorous acid of the invention are not contained, or, chlorite-containing preparations were produced which contained practically only chlorite so that they are unsuitable for pharmaceutical applications.

Because large amounts of chlorite are detrimental to the use of dichloric acids according to the invention in the pharmaceutical sector, it is especially advantageous if the end-product of the solutions, according to the invention, do not contain chlorite in more than 20-fold excess, preferably in not more than 5-fold excess and even more preferably in not more than a 3-fold excess in percentage by weight related to the total weight of the solution.

In particular, the dichloric acids and peroxochlorous acid according to the invention are present in this solution in volumes of about 0.1-20 weight %, preferably 3-5 weight %, related to the percentage by weight of the $ClO_2$ employed. The qualitative detection is successful using Raman spectroscopy. The performance of this type of spectroscopy is a matter of course for an expert in this field. The spectrograms which are obtained clearly differ from those which are obtained with the process described in WO 00/48940. The determination of the quantitative share can be carried out using titration.

A further qualitative detection is possible using the reaction with the heme iron. In the presence of the dichloric acids of the invention, the temporal course of the change in intensity of the Soret bands is clearly different to the results of the solutions which were obtained with the process described in WO 00/48940.

The process according to the invention consists of a reaction of chlorine dioxide with an aqueous or water-containing hydrogen peroxide (or another hydroperoxide or peroxide known to an expert, such as e.g. peroxocarbonate, or perborate, or the urea adduct of the hydrogen peroxide) at a pH value of 6.5 or greater, preferably pH 10-12. Preferably, the pH value should be kept at a constant level.

Moreover, surprisingly, it has been shown that peroxochloric acid, which occurs as an intermediate product, as well as its anions and derivatives, can also be obtained by the reaction of chlorine dioxide with other oxidants which contain the peroxo group.

The reaction can be carried out in an aqueous environment or a water-containing environment. For example, as well as water, solvents can be present which are miscible with water such as alcohols or alkanols such as methanol, ethanol or mixtures of these.

Alternatively, other chlorine oxides can be used initially. For example, chlorine monoxide, preferably in its dimeric form ($Cl_2O_2$), can also be converted with a hydroperoxide (preferably hydrogen peroxide) to the desired product. The reaction is successful in the same pH range as stated for chlorine dioxide.

The reaction temperature can be increased for example up to about 50° C.; in purely aqueous systems, the lowest temperature should be preferably about 0° C. One should not work with chlorine dioxide under +10° C. however, because the chlorine dioxide gas liquefies below this temperature and deflagration can occur. If additional organic solvents and/or high concentrations of the active reagents are present, then lower temperatures, i.e. below the freezing temperature of water, can be used. Preferably, work takes place at room temperature.

The chlorine dioxide required for the reaction is available to experts and can be manufactured in the usual way. For example, it can be manufactured by the reaction of a chlorite with an acid (e.g. sodium chlorite with sulphuric acid) or by the reduction of chlorate—for example with sulphurous acid.

The chlorine dioxide thus obtained can be liberated in the usual manner—if necessary after removal of traces of chlorine (Granstrom, Marvin L.; and Lee, G. Fred, J. Amer. Water Works Assoc. 50, 1453-1466 (1958)).

If the chlorite used to make $ClO_2$ is contaminated with carbonate, the $ClO_2$ will be contaminated with $CO_2$ and/or the carbonic acid adducts described in WO 00/48940. In order to absorb the carbon dioxide, the gas stream containing chlorine dioxide and carbon dioxide should be directed through a washing bottle filled with a lye. During short contact times, the $CO_2$ but not the $ClO_2$ will be absorbed by the lye. It is preferable, however, to remove the carbonate contamination by fractioned crystallisation of the sodium chlorite which is used. A contamination of the peroxochlorate with carbonate can be easily recognized on the Raman spectrum. Instead of sharp bands at 1051 $cm^{-1}$, one obtains a double band 1069 $cm^{-1}$ (wide) and the important bands, within the scope of the invention, at 1051 $cm^{-1}$ (sharp).

The chlorine dioxide can be transported with an inert gas such as nitrogen or with a rare gas such as argon, however, air or oxygen for the reaction with the peroxo compound or the hydroperoxide such as hydrogen peroxide or perborate can also be used. For example, it is possible to make the chlorine dioxide in a first reaction vessel and then to introduce it with the above mentioned gases or mixtures of them into a second reaction vessel which contains the peroxo compound (peroxide or hydroperoxide) in an aqueous or water-containing solution.

The pH value of the reaction mixture is kept equal to, or above, 6.5 by adding a base. It is preferable to keep the pH value constant. This can be carried out either manually or by using a pH "stat".

The usual organic or inorganic bases can be used such as bases, for example caustic soda solution or caustic potash solution or alkaline-earth hydroxides as well as ammonia; or organic bases such as nitrogenous bases. Furthermore, the hydroxides from of quaternary ammonium salts in particular alkyl, trialkyl or tetraalkyl ammonium hydroxide, or zinc hydroxide can also be used.

The content of hydroperoxide in the reaction mixture can, for example, be determined using potentiometric titration with an acid such as hydrochloric acid.

The solutions obtained according to the procedures described above can be used in both the form in which they were made or in variations of this. For example, superfluous hydrogen peroxide can be removed in the usual way, e.g. with a heavy metal compound such as manganese dioxide. Surpluses of the other oxidants can be removed with similar means.

Surpluses of chlorine dioxide ($ClO_2$) can be removed with $H_2O_2$. This should take place as soon as possible, otherwise via

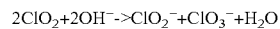

$$2ClO_2 + 2OH^- \rightarrow ClO_2^- + ClO_3^- + H_2O$$

disturbing $ClO_3^-$ with pentavalent chlorine (chlorate) will be formed. A product containing chlorate is however undesirable.

In order to improve the storage life of the reaction product, storage at a high pH value is suitable, for example, pH 10 and above. The adjustment of this pH value can be carried out with a suitable base—as described previously in the manufacturing procedure.

In the manufacture of solutions which contain the dichloric acids and/or the salts of these acids, surprisingly, it is possible to expel and collect the free acid HOOClO, the dichloric acids or the peroxochloric acid out of the mixture containing chlorite ions with an inert gas such as a noble gas, e.g. argon, or with nitrogen or with the gases oxygen or air, while lowering the pH to below 6, e.g. pH 5, or less. Surprisingly, it has been demonstrated that the yield can be enormously increased if the gas stream distance is kept very short and the stream is cooled.

The mixture which forms after the start of step (a) in the manufacturing procedure described above contains, at first, very high concentrations of chlorite ions ($ClO_2^-$). The chlorite content, however, can be considerably reduced by the "passing over" in a gas stream in a basic solution. In this process, all types of chloric acids are expelled as volatile compounds in protonated (neutral) form. These are however very instable. A base is present in the receiving vessel through which the chloric acids are deprotonated and the anions are formed. After the solution has been adjusted to pH 6-8, and after defined volumes of chlorite—for example, in the form of sodium chloride—have been added, the anions of the dichloric acids are formed.

Collection can be carried out, for example, in a base, such as an alkaline metal base, alkaline-earth metal base or a zinc base or nitrogenous base such as ammonia or an organic amine. It is also possible to freeze out the gaseous acids in a cold trap (e.g. at −100 to −190° C.).

Counterions can be all metal cations and organic cations such as those from nitrogenous bases, in particular quaternary ammonium salts. The choice of the most suitable cations can be determined from the individual purpose of use. For pharmaceutical applications, alkaline earth or alkaline metals, preferably Na$^+$ or K$^+$, or Zn$^{2+}$ are most suitable. In technical applications, organic cations, such as cations from nitrogenous bases, in particular alkyl ammonium cations such as trialkyl ammonium cations or especially quaternary ammonium cations can be used.

It is appropriate and preferable to store the acid and the salts, according to the invention, in the dark and to make aqueous solutions with high pH values out of them, e.g. with pH values of 10, 11 or 12 and above, in particular the range of pH 10 to pH 13, in order to ensure a long storage life. Depending on the need, the free acid can be regained from such solutions in the manner described previously and, if necessary, can be converted to solutions with the desired pH value or into salts.

The dichloric acids according to the invention, their derivatives or anions and salts of these, can be used as they are, but particularly also in aqueous or water-containing solutions, as oxidants for very different medical, cosmetic, technical and agricultural purposes.

Examples for possible test systems are included in the initially named publications and patent documents, which are included herein in this respect by reference.

An application possibility exists in the use as pharmaceutical preparations (medicaments), or for the manufacture of medicaments, which can be administered in all possible methods, in particular topically but also parentally. The medicament can be formulated in the usual way with the usual pharmaceutically well-tolerated vehicles and diluting agents.

The invention also relates to pharmaceutical preparations which incorporate the dichloric acids or peroxochlorous acid, respectively, according to the invention, their anions, derivatives or salts as the active substance and which can be used in particular to treat the illnesses mentioned in the introduction. Especially preferential, are preparations for enteral administration such as nasal, buccal, rectal and especially oral administration (preferably avoiding the acid of the stomach, e.g. gastric juice-resistant preparations such as capsules or coated tablets), as well as particularly for local or parenteral treatment, such as intravenous, intramuscular or subcutaneous administration to homothermal animals—in particular humans. The preparations contain the active substance alone or preferably together with one or more pharmaceutically applicable vehicle materials. The dosing of the active substance depends on the illness being treated as well as the species being treated, its age, weight and individual condition, individual pharmacokinetic circumstances as well as the method of application. Preferably, the dosage for the enteral or particularly the parental administration (for example by infusion or injection) (most favourably in humans) lies in the range of 0.01 to 100 pmol/kg, in particular between 0.1 and 100 pmol. Therefore, for example, a person with a bodyweight of 70 kg should receive 1 mg to 1 g/day, in particular between 8.5 mg and 850 mg/day, administered in one dose or split up into several smaller doses. For local application, the preferable dosage range lies between 0.1 and 10, in particular between 0.5 and 5 mL/100 cm$^2$ of a 0.1 to 10 millimolar solution (correspondingly more or less for larger or smaller surfaces—either applied directly or using, for example, bandages out of impregnated gauze).

Thus the invention also relates to a method—for the prophylactic and/or therapeutic treatment of the pathological conditions described here, in particular for the prophylactic and/or therapeutic treatment of diseases where a strengthening of tissue regeneration, an immunomodulation, an improvement of vaccination reaction or a radiation sensitization is indicated and successful, or one or more of these effects, in particular in the treatment of wounds in warm blooded animals—incorporating the administration of the dichloric acids or peroxochlorous acid, respectively, its anions, derivatives or salts, according to the invention, in an effective dosage against the aforementioned diseases to a warm blooded animal, e.g. a human being who requires such a treatment.

The invention also relates to a pharmaceutical composition—for the prophylactic, and in particular, for the therapeutic treatment of the disease conditions described here, preferably for the prophylactic and/or therapeutic treatment of diseases where a strengthening of tissue regeneration, an immunomodulation, an improvement of vaccination reaction or a radiation sensitization is indicated and successful, or for one or more of these effects, in particular in the treatment of wounds, preferably of a warm blooded animal who is suffering from such a condition—which contains dichloric acids or peroxochlorous acid, respectively, its anions, derivatives or salts, according to the invention, in a prophylactically, or in particular, therapeutically effective dosage against the aforementioned diseases and one or more pharmaceutically applicable vehicle materials.

The invention also relates to a procedure—for the treatment of pathological conditions preferably for the prophylactic and/or therapeutic treatment, in particular of a warm blooded animal, especially a human being, where a strengthening of tissue regeneration, an immunomodulation, an improvement of vaccination reaction or a radiation sensitization is indicated and successful, in particular in the treatment of wounds in warm blooded animals—which incorporates the administration of the dichloric acids, or peroxochlorous acid, respectively, its anions, derivatives or salts, according to the invention, in an effective dosage against the aforementioned diseases to a warm blooded animal, e.g. a human being who requires such a treatment.

The invention also relates to the use of the dichloric acids and/or the peroxochlorous acid and their derivatives, anions or salts, according to the invention, in a procedure for the treatment of an animal or human body.

Therefore, the invention also relates to the use of the dichloric acids and/or the peroxochlorous acid and their derivatives, anions or salts, according to the invention, preferably for prophylactic and/or therapeutic treatment of diseases, in particular of a warm blooded animal, especially a human being, where a strengthening of tissue regeneration, an immunomodulation, an improvement of vaccination reaction or a radiation sensitization is indicated and successful, in particular in the treatment of wounds.

The invention also relates to the use or a method for the use of the dichloric acids and/or the peroxochlorous acid and their derivatives, anions or salts, according to the invention, for the (cosmetic) care of the skin, for example when a person has a tendency to develop spots and pimples (e.g. acne) or if pimples are present.

Dosage unit forms are e.g. dragees, tablets, ampoules, vials, suppositories or capsules. Further administration forms, in particular for solutions of the dichloric acids and/or the peroxochlorous acid and their derivatives, anions or salts, according to the invention, are e.g. ointments, creams, pastes, gels, foams, mouthwash, drops, sprays and similar. The dosage unit forms, e.g. ampoules, tablets or capsules, contain preferably between about 0.05 g to about 1.0 g, in particular from 8.5 mg to 850 mg, of a salt of the dichloric acids their anions or derivatives according to the invention with the usual pharmaceutical vehicle materials.

The pharmaceutical preparations of the invention were essentially manufactured in the known manner, e.g. using conventional mixing, granulating, coating, dissolving or lyophilising methods.

In a preferential experimental procedure, a 0.05 to 1 M solution of a dichloric acid salt or the peroxochlorous acid and/or a salt of its derivatives can be dissolved in bidistilled water at a pH equal to or >10, preferably 10 to 13, in particular 12.5. Immediately before administration, this solution is diluted with common salt, sodium or potassium bicarbonate and bidistilled water to isotonie in concentrations of about 1-5 mM approaching the physiological pH. This solution is suitable for parental, preferably intravenous application.

In order to make a preferential formulation of a drug for topical use, the method of choice is to dissolve the dichloric acids and/or the peroxochlorous acid or their derivatives, according to the invention, as salts in bidistilled water with concentrations in the lower millimolar or in the upper micromolar range—preferably in the concentration range of 0.5-5 mM with the pH equal to or >10, in particular 10 to 13, most preferably e.g. pH 11.5 and adjust the solution to isotonie with glycerine or common salt or another suitable well-tolerated, preferably physiological agent. Before application, a physiological pH is set with HCl. Further additives are possible. In particular, in connection with the filling of the medicament into plastic containers, such additives are suitable which can neutralise traces of transition-metals, because, during storage, transition-metals in the walls can be dissolved and can catalyse a degradation of the active substance. Examples of such additives are oligo and polyalcohols, such as ethylene glycol, desferrioxamine or EDTA (e.g. as disodium EDTA). The solution which is obtained in the above manner can also be applied directly to wounds.

The anions of the dichloric acids or peroxochlorous acid according to the invention are stable, the acids themselves decompose relatively quickly. Therefore, an active substance stabilisation can be carried out using the pH. In order to improve tolerance, the active substance solution can be lowered to an almost physiological pH by buffer dilution immediately before use. This is adequate for a deployment of the pharmacological action throughout the body, because this action does not rely on the receptor-ligand interaction of a conventional drug, but it is, as previously stated, related to a fast and irreversible oxidation reaction. The pharmacological action remains in effect as long as the cell and/or its chemically changed structures are present, i.e. it is not terminated after diffusion of an active substance from a receptor.

Examples for indication fields in which an enhancement of tissue regeneration is successful, either prophylactically or in particular therapeutically, for the treatment of a pathological condition are the regeneration after physical damage (e.g. traumatic contusions or lacerations, short-wave rays, radio-active radiation) and after chemical damage (e.g. through tissue poisons, such as Lost, chemotherapeutic agents). A further application area in this field is the improvement of wound healing—in particular stubborn so-called "spontaneous" wounds—which occur as a result of a primary disease (e.g. Diabetes mellitus, vascular disorders, immunosuppression or the result of old age) and which will not heal. Outstanding examples of such disorders are bedsores and chronic varicose ulcers. Here, wound treatment is to be understood as treatment of wounds of the skin, mucous membranes and other tissues such as e.g. liver, myocardium or bone marrow.

Because the dichloric acids or peroxochlorous acid according to the invention are defined compounds, there are no related difficulties in new drug approval.

Here, a growth stimulating effect of 20-25% of the trial solution 1, which includes both dichloric acids according to the invention and also chlorite, is clearly recognisable in the cell culture which, in relation to the controls, is significantly higher.

The application of the solutions containing only RC or chlorite shows exactly how the controls have no effect whatsoever on the growth behaviour of the fibroblasts.

Figure 2:
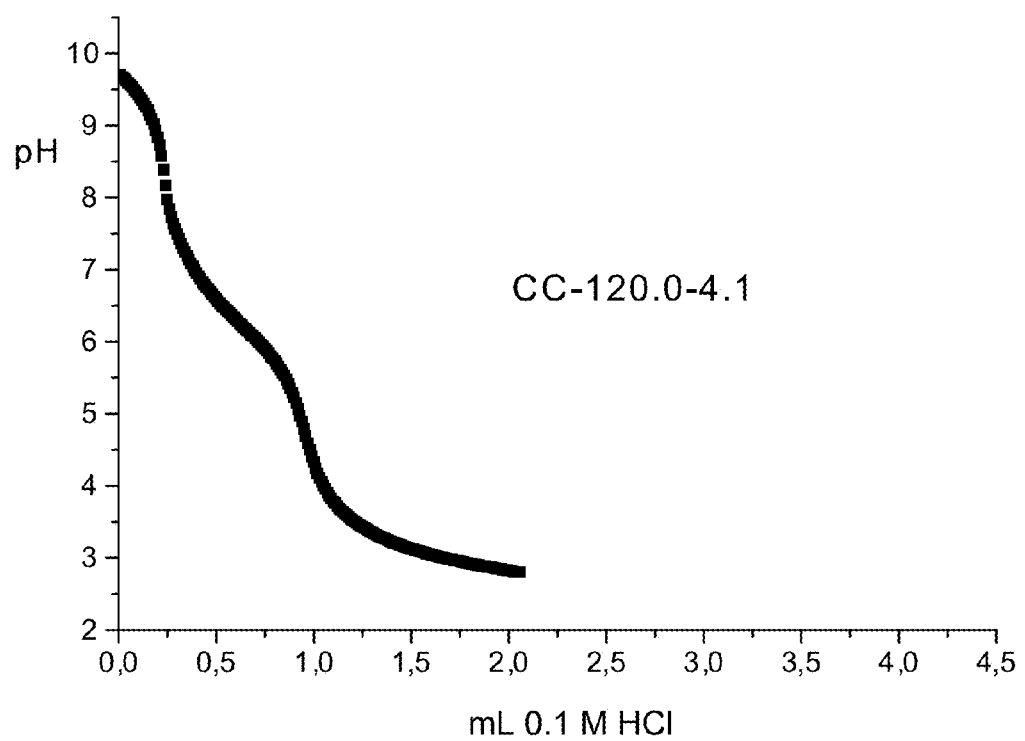
Figure 3:
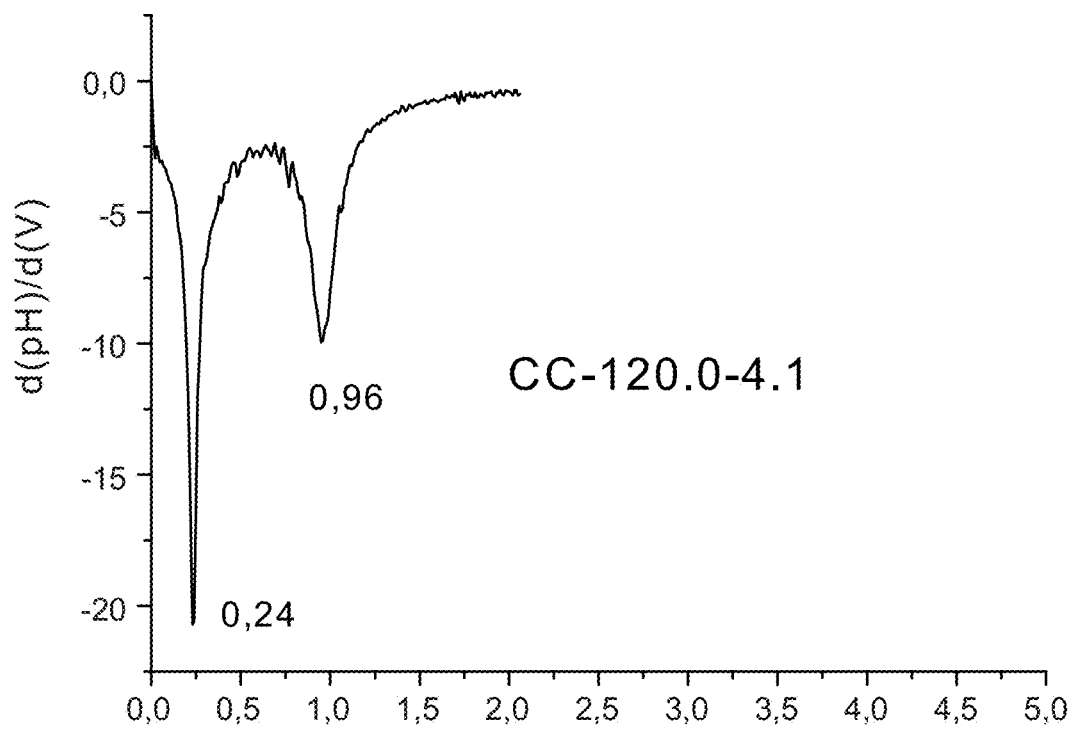

FIG. 2 shows the titration of the anions of the peroxo acids (dichloric acid, peroxochlorous acid) present in the solution to determine the concentration of the acid ions. In FIG. 3, the titration curve derived from FIG. 2 is shown which provides exact concentration determination.

Figure 4:
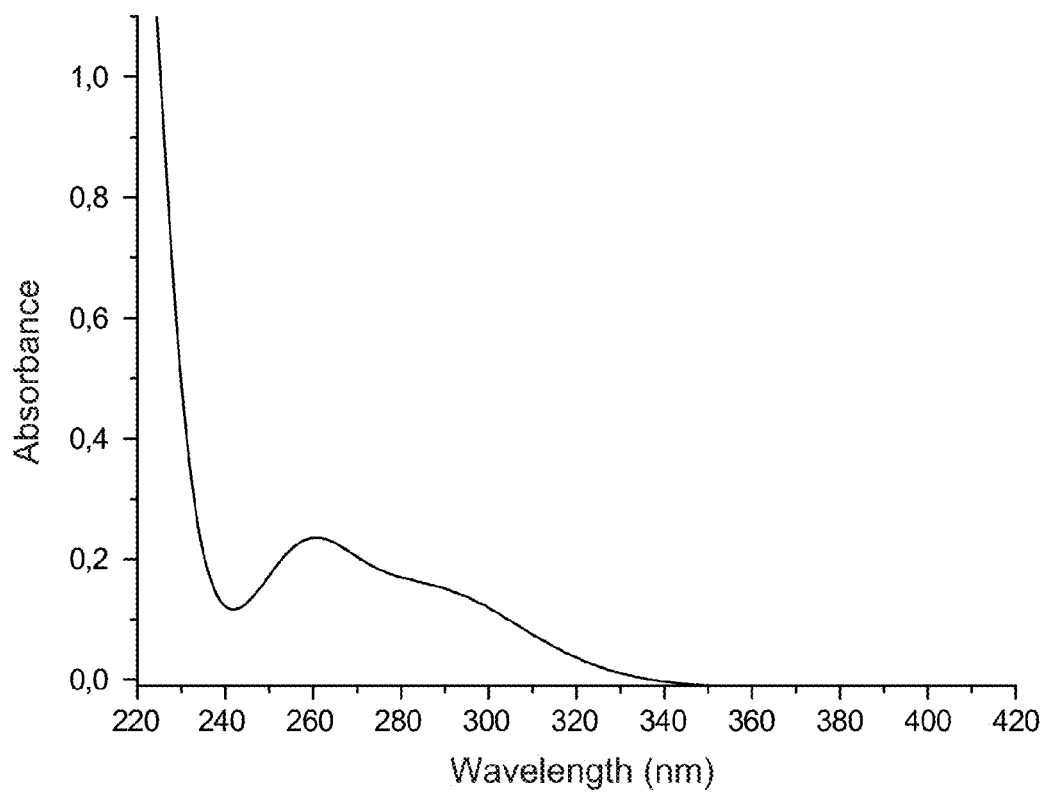
Figure 5:
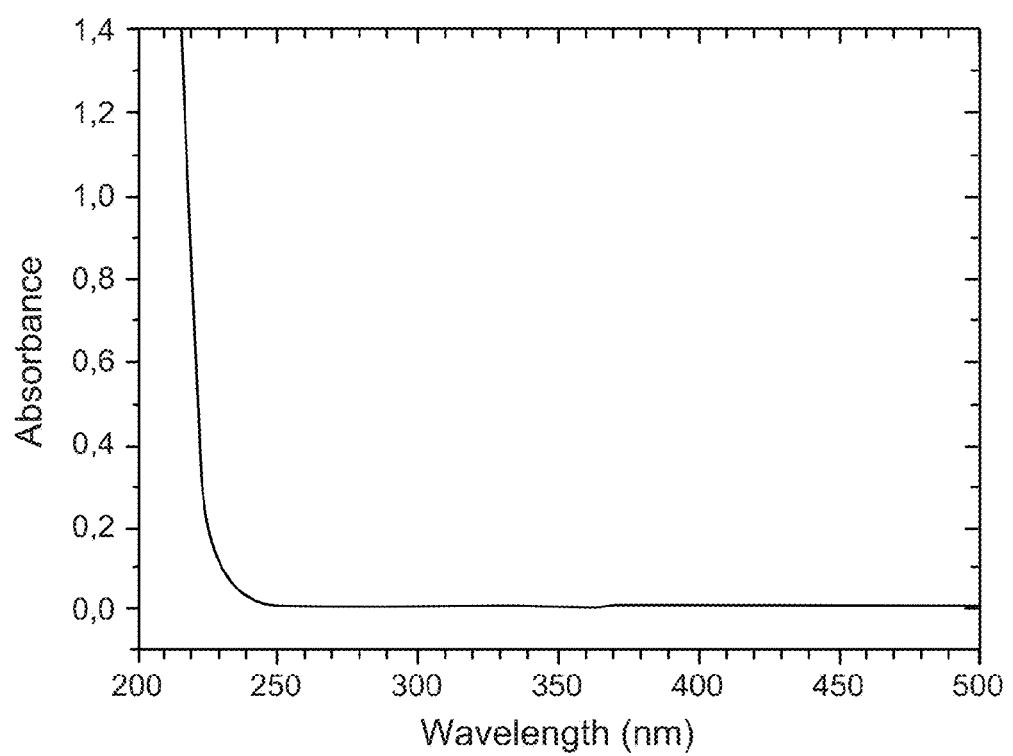

FIGS. 4 and 5 are examples of UV spectra. The UV absorption measurements permit the determination of the chlorite concentration and show any dissolved free chlorine dioxide which may be present.

Figure 6:
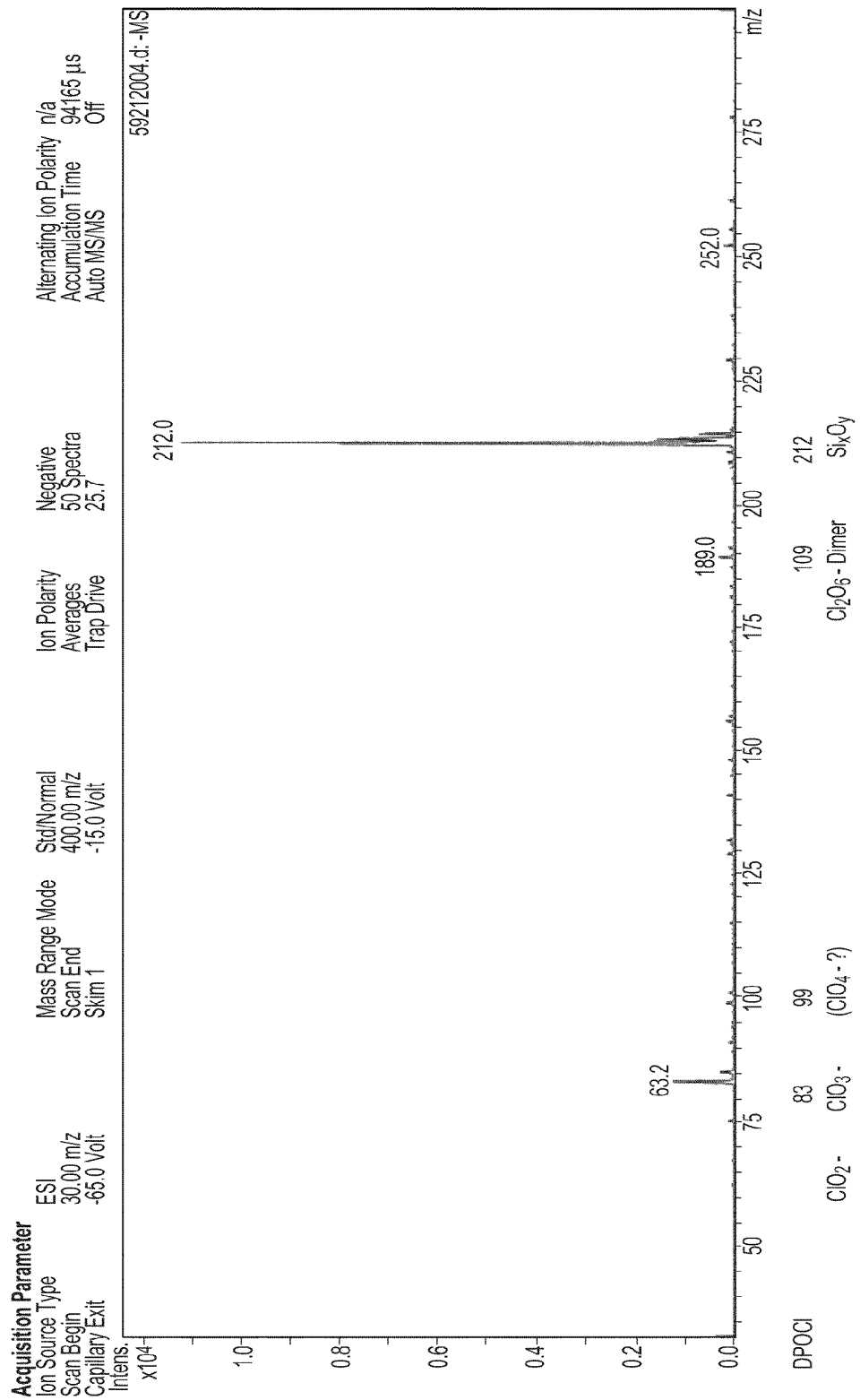

FIG. 6 shows a mass spectrum of the product solution whereby the peroxochlorite (mass 83.2) and the anion of the dichloric acid (mass 189) were identified.

Figure 7:
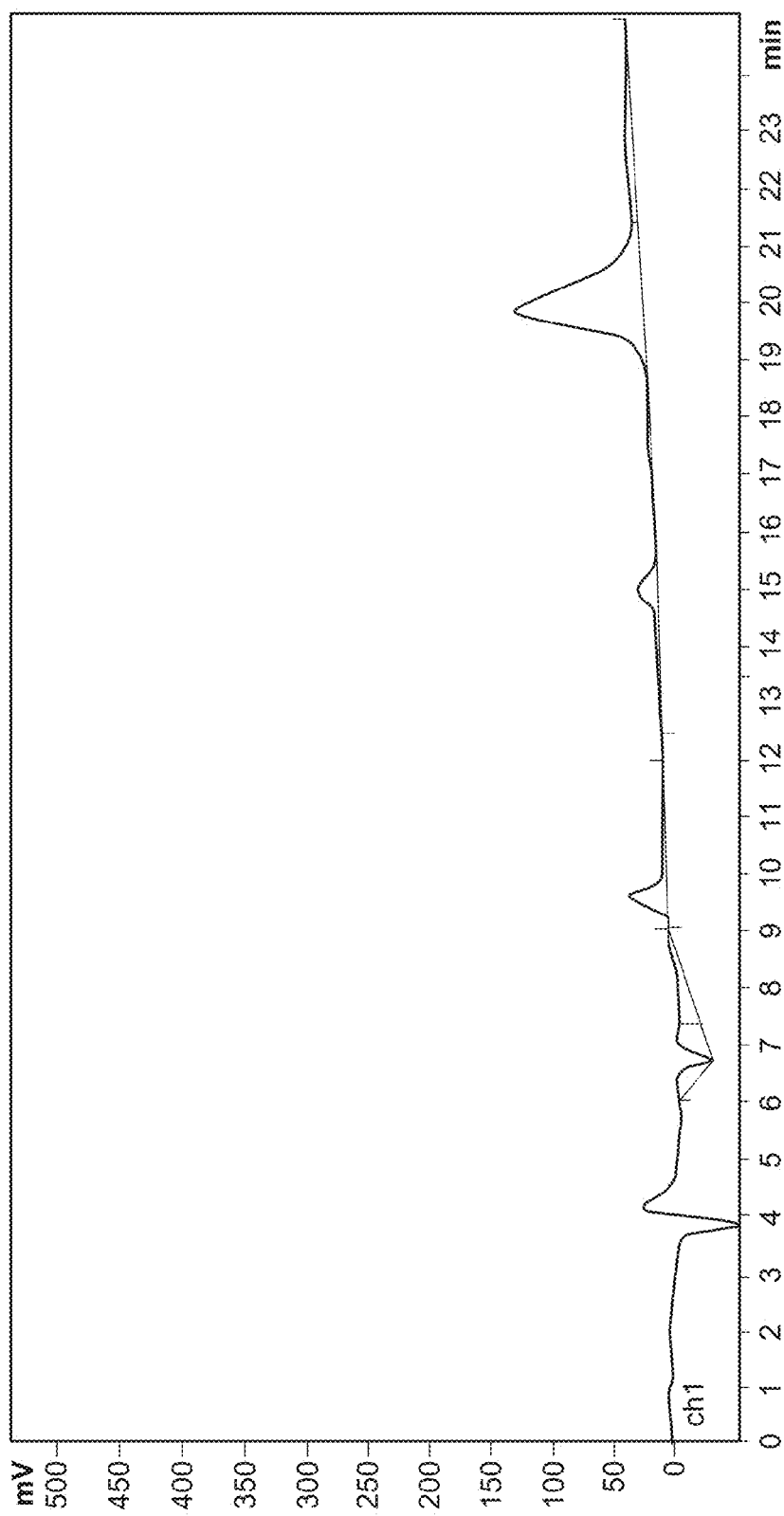

In FIG. 7, the results of an ion chromatography are shown. The retention times of reference substances are provided in Example 4 part 5. The dichloric acid is detected at 19.77 min, whereby no chlorate ($ClO_3^-$) is determined which excludes chlorate as the cause of the peak in the mass spectrum at 82.3 in FIG. 6.

Figure 8:
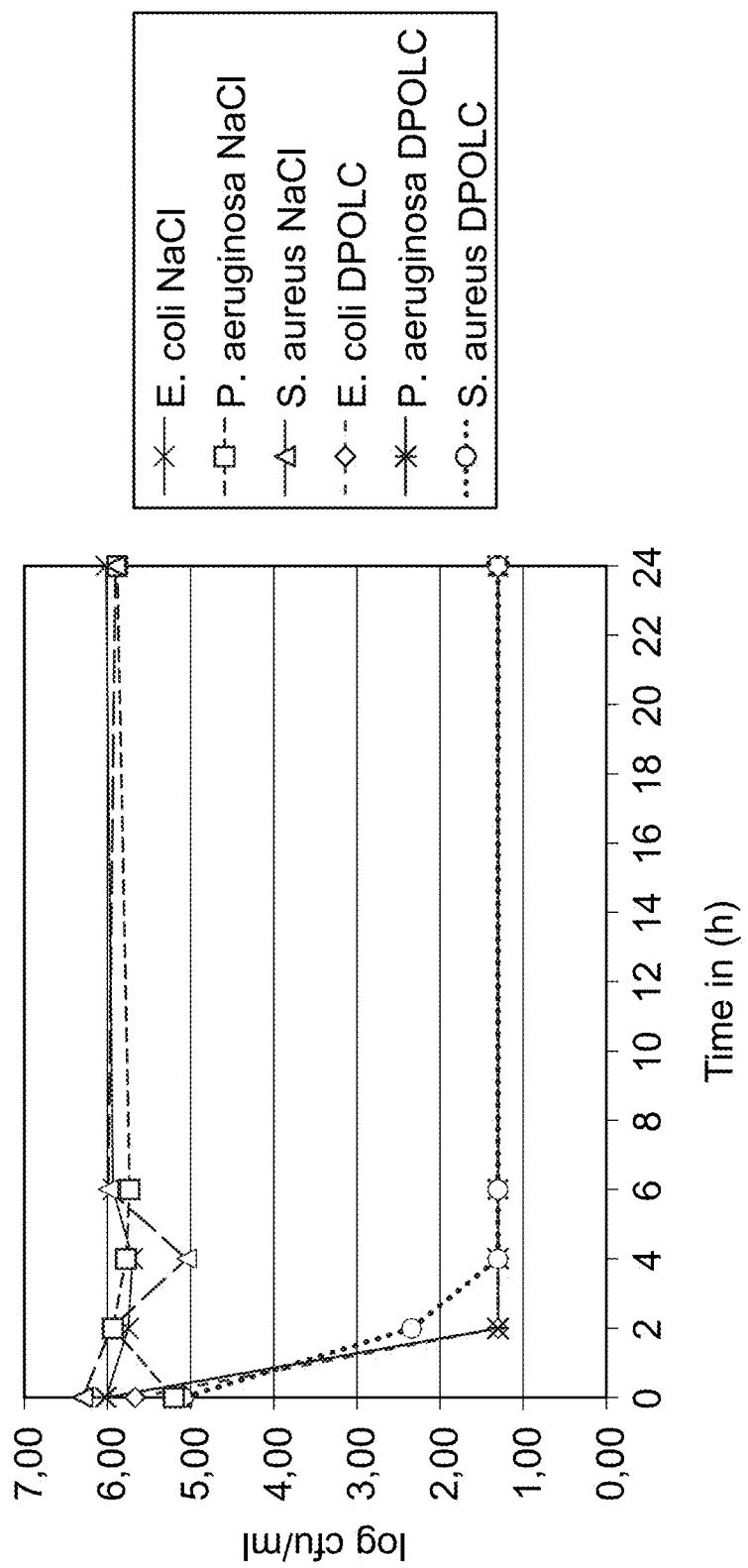

FIG. 8 shows decay rate kinetics with three bacteria strains, *E. coli*, *S. aureus* and *P. aeruginosa*. In all three strains, a bactericidal action according to DIN 58940 was obtained with the product solution.

DETAILED DESCRIPTION

The following examples provide more details about the invention, these should however by no means be understood in a limiting sense.

EXAMPLES

Example 1

Preparation of the Dichloric Acids

Carefully, drop for drop, sulphuric acid (96%) is stirred into a solution of 100 g anhydrous sodium chlorite in 200 mL water. The chlorine dioxide which forms is expelled using a strong gas stream (Ar, $N_2$ or $O_2$ or $CO_2$-free air). The gas stream must be so strong that the content of $ClO_2$ does not exceed 5% (danger of explosion). In order to trap elemental chlorine, the gas stream containing $ClO_2$ is introduced into three washing bottles attached to each other which are each filled with 30 mL of a 2 M $NaClO_2$ solution at pH 11, in a solution of 15 mL of 30% hydrogen peroxide in 35 mL of water, which had previously been adjusted to pH 12 by adding 4M caustic soda solution. A solution of sodium perborate or sodium percarbonate or another peroxo compound, such as e.g. the $H_2O_2$ adduct of urea can be used instead of hydrogen peroxide. During the introduction of the gas, the pH value is controlled with a glass electrode. By adding 4M NaOH, the pH value during the reaction can be kept at 12. The hydroperoxide or peroxo compound are exhausted when the inflow of gas leads to a permanent yellow coloring. A drop of the solution of the oxidant (e.g. $H_2O_2$) will subsequently decolorize the yellow solution again.

While stirring, the solution containing reactive chlorine is dripped into a solution of 500 g citric acid in 3 liters of water which has previously been adjusted to pH 4.5 with 2 M caustic soda solution. During this addition, the reactive chlorine compound which forms is expelled with a strong gas stream ($N_2$ or $O_2$). Preferably, the gas stream should be cooled. The tube connections should be as short as possible. The gas is collected, for example in three washing bottles which are attached behind each other and which are each filled with 50 mL 0.1 M NaOH.

The contents of the three washing bottles are combined and kept at pH >10.

In order to form the dichloric acids according to the invention, the pH is adjusted to 7—for example with hydrochloric acid—and a 10-fold molar excess of sodium chlorite is added. For storage, preferably, the pH should be adjusted to about more than 10 up to about 13.

The total content of reactive chlorine anions is determined by potentiometric titration with 0.1 M HCl with the usual method known to the man skilled in the art.

The dichloric acids which are formed are present in solution in a mixture with a defined volume of chlorite as well as further reactive chlorine compounds.

The presence of the dichloric acids is detected with Raman spectroscopy.

Example 2

Cultivation of MRC 5 Fibroblasts

Solutions:
Culture Medium for MRC 5:
   89 mL IF basal medium
   10 mL FCS (foetal calf serum)
   1 mL L-glutamine stock solution
IF Basal Medium
   The IF basal medium is a 1:1 mixture of IMDM (Iscove's Modified Dulbecco's Medium) and Ham's F12 medium
L-glutamine Stock Solution
   200 mM L-glutamine are dissolved in IF basal medium and sterilized by filtration.
Cultivation:
   The MRC 5 cell line used is seeded in non-gelatine coated cell culture dishes. The subsequent cultivation is carried out in an incubator at 37° C. and 5 vol % $CO_2$ in a water vapor saturated atmosphere. Every second to third day, the culture medium is changed and after confluence is reached the cells are passaged with a separation rate of 1:5 to 1:10.

Example 3

Cell Biological Test of Active Substance

Solutions:
Culture Medium for MRC 5:
   89 mL IF basal medium
   10 mL FCS (Foetal Calf Serum)
   1 mL L-glutamine stock solution
Serum-Reduced Culture Medium for MRC-5:
   98 mL IF basal medium
   1 mL FCS (Foetal Calf Serum)
   1 mL L-glutamine stock solution
PBS (Phosphate Buffered Saline):
   140 mM NaCl, 3 mM KCl, 8 mM $Na_2HPO_4$ and 1.5 mM $KH_2PO_4$ are dissolved in water, whereby a pH value of 7.2-7.4 is set. The solution thus obtained is sterilized by autoclaving.
Cell Lysis Buffer
   0.04% SDS (stock solution 10% SDS)
   2×SSC (stock solution 20×SSC)
   to obtain 25 mL of finished cell lysis buffer, 5.0 mL 20×SSC and 100 µL 10% SDS are filled up to 25 mL with PBS.
DAPI Solution
   2 µM DAPI in PBS
Cultivation:
   The MRC 5 cells are seeded at 400 cells/cm² in a 24 well cell culture plate. The subsequent cultivation is carried out in an incubator 37° C. and 5 vol. % $CO_2$ in a water vapor saturated atmosphere. After 24 hours of precultivation, the culture medium is suctioned off and the cells are washed with PBS. The culture medium is then changed to serum-reduced culture medium and the active substances to be tested (the following table shows an overview) are added.

After 24, 48 and 72 hours, the proliferation of the cells is determined by quantification of the cellular DNA in a fluorometer (Novostar-Company: BMG Labtechnologies) after DAPI staining. Here, the increased fluorescence in the samples is equal to a proliferation of the cells.

The plate to be measured is washed once per well with 500 µl PBS and then 250 µl PBS is placed in each well. 250 µl lysis buffer are added and the cells are lysed in a shaker at the lowest setting for 30 min at RT. Subsequently, 500 µl DAPI solution is added and the plate is left to stand for a further 10 min at RT.

The plate is measured at 355 nm ex. and 460 nm em. in the Novostar. Normally, work is carried out with a gain adjustment of 1400-1600.

The multiple determinations are averaged and the error values are calculated. The data obtained is evaluated graphically.

The following stock solutions are used:

TABLE 2

Combination of the active substances used
[Concentration of the stock solutions]

| Designation | Content of [mM] | Content of chlorite [mM] | Comment |
|---|---|---|---|
| Control | — | — | Serum-reduced culture medium |
| Sample 1 | 40 | 6 | in serum-reduced culture medium |
| Sample 2 | 40 | — | in serum-reduced culture medium |
| Sample 3 | — | 6 | in serum-reduced culture medium |

Observed Growth Stimulation of Fibroblasts:

For use in the cell culture, the solutions are first diluted in the given culture medium. The results shown in FIG. 1 were obtained with active substance concentrations of 100 µM chlorite and 50 µM of the RC (=mixture of the dichloric acid and the peroxochlorous acid, according to the invention, or the anions thereof).

Here, a growth-stimulating effect of 20-25% of the sample solution 1, which contains both RC and also chlorite, is clearly recognisable and this is also significantly higher in relation to the control.

Example 4

Analytical Determination of the Solution Obtained from Example 1

1) pH measurement:

The pH measurement is made with a single-rod glass electrode. The product content and the position of the equilibrium is dependent on the pH value.

2) Titration with 0.1 M HCl:

The titration serves for example for the quantitative determination of the dichloric acid content or also the content of peroxochlorous acid or the peroxochlorate.

1 mL each of the product solution are titrated potentiometrically with 0.1 M hydrochloric acid. The titration curves are recorded (pH vs. mL 0.1 M HCl). From the acid consumption measured in the derivation of the titration curve between pH 8.5 and 4.5, the anion content from the corresponding acids is determined as a sum.

In a typical result, 1 mL product solution results in a consumption 0.72 mL 0.1 M HCl and thus a concentration of 0.072 M.

FIG. 2 shows a recorded titration curve:

The derivation of the titration curve and the determination of the concentration are shown in FIG. 3.

Figure 1:
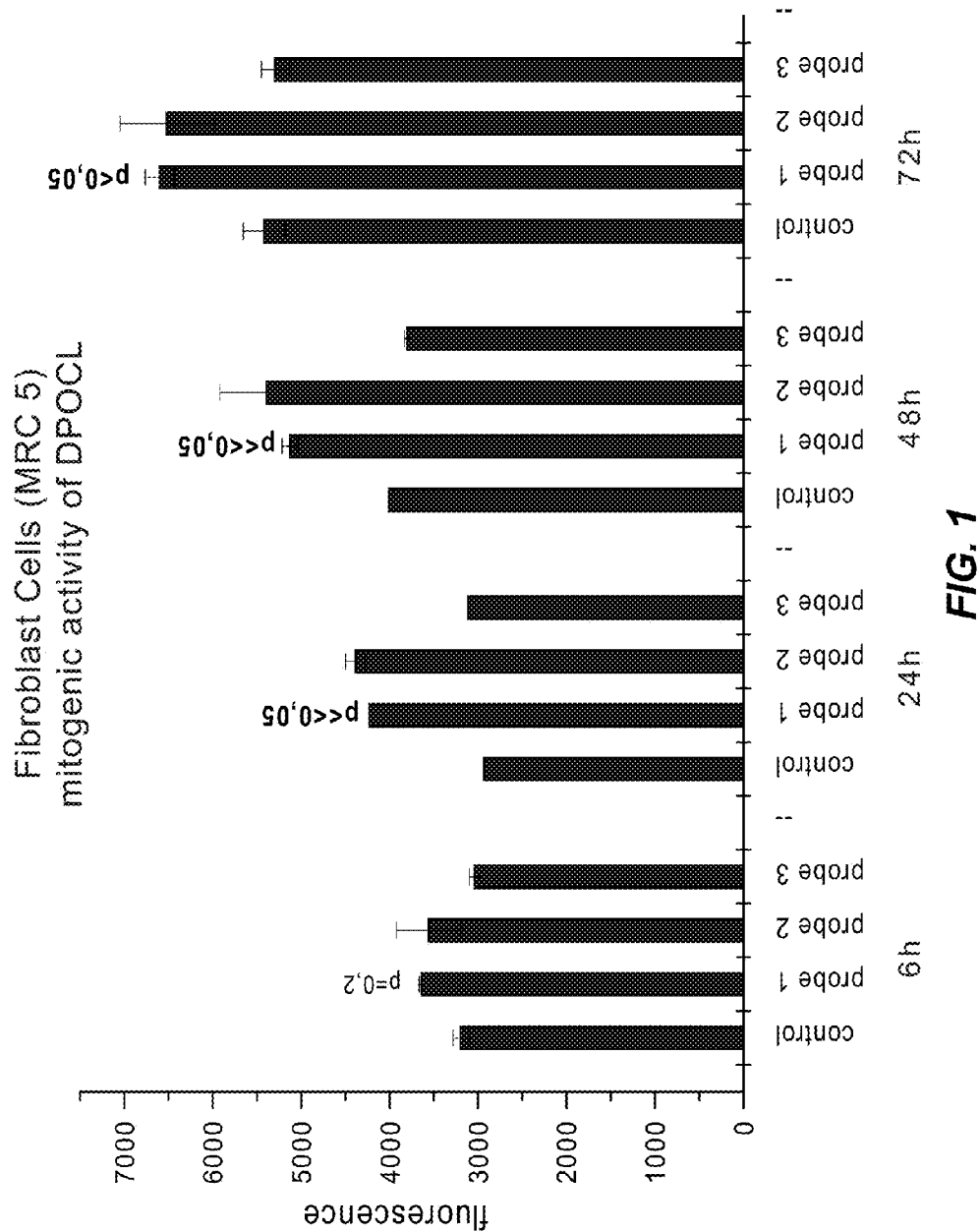
FIG. 1 shows the results of the cell culture experiments (stimulation of growth of fibroblasts) as shown in Example 3. These were obtained with active substance concentrations in the culture medium of 100 µM chlorite and 50 µM of reactive chlorine (RC=sum of the anions of all dichloric acids and the peroxochlorous acid).

3) UV-Vis absorption spectrum:

The measurement of the UV spectrum serves the quantification of the chlorite content in the product solution. For comparison, FIGS. 1 and 5 show spectra of a chlorite-containing and a chlorite-free product solution. The chlorite signal is seen at 260 nm; chlorine dioxide, which originates from the process, shows a signal at 360 nm.

The absorption values are determined at 260 nm and 500 nm in 1 cm quartz cuvettes. The $ClO_2^-$ ion content is determined from the difference A260-A500 and with the help of the extinction coefficient for chlorite of $\epsilon 260\ nm = 140\ M^{-1}\ cm^{-1}$ at 260 nm.

An absorption at 360 nm suggests free chlorine dioxide ($\epsilon 360\ nm = 1260\ M^{-1} cm^{-1}$).

4) Mass Spectroscopy

The ESI mass spectrometry was carried out with a Bruker Esquire-LC spectrometer in the standard MS mode. The sample was an aqueous product solution which had been diluted with methanol before the measurement. The scan range used lay between 30 m/z and 400 m/z with capillary exit −65, voltage and skim −15 V; the spectrum represented an average value from 50 measurements.

The arrow on the right in FIG. 6 points to the signal of the dichloric acid (sum formula: $Cl_2O_6^{2-}$), the arrow on the left shows the previously unknown peroxochlorite species (sum formula: $ClO_3^-$).

5) Ion Chromatography

All analyses were carried out with a modular ion chromatography system from the Metrohm company.
Pump: Metrohm IC 709 Pump
Detector: Metrohm 732 IC Detector
Suppressor: Metrohm 753 Suppressor Module
Column: Metrosep A 250
Flow rate: 1 ml/min
Injection volume: 20 μL
Eluent: 1 mM NaOH Immediately before each measurement, known concentrations of the reference substances were freshly prepared. These were then measured with the method described above and with the eluents stated.

Retention times of the reference substances:

| Substance | Retention time [min] |
|---|---|
| NaCl | 13.21 |
| $NaClO_2$ | 12.30 |
| $NaClO_3$ | 16.26 |
| $NaClO_4$ | 4.36 |
| NaOH | 17.32 |
| $Na_2CO_3$ | 21.98 |
| $Na_2Cl_2O_6$ | 19.77 |

FIG. 7: In the ion chromatography, the dichloric acid shows a typical peak as a retention time of 19.77 min. None of the known reference substances could be detected. The ion chromatography confirmed the findings of the mass spectroscopy. A chlorate-typical peak ($NaClO_3$, retention time 16.26 min) cannot be detected in the solution prepared according to Example 1. Therefore, the peak with the sum formula $ClO_3^-$ in the mass spectroscopy (FIG. 6, mass 83.2) can only be the new peroxochlorous acid or anions thereof.

Example 5

Bactericidal Action of the Solution Obtained from Example 1

Decay kinetics according to DIN 58940
Solution according to Example 1 was used in a 1:10 dilution.

Test organisms: *Escherichia coli* ATCC 25922, *Pseudomonas aeruginosa* ATCC 27853, *Staphylococcus aureus* ATCC 29213

Nutrient medium: Casein peptone—Soya peptone (Ph.Eur.2.6.12)

Bacteria incubation time: 18 h +/−1 h

The result is shown in the following Table 3 as well as in FIG. 8. Thus, the bactericidal action of the solution used has been proved according to DIN 58940.

TABLE 3

| Time (h) | E. coli | | NaCl | P. aeruginosa | | NaCl | S. aureus | | NaCl |
|---|---|---|---|---|---|---|---|---|---|
| | cfu/ml | log cfu/ml | | cfu/ml | log cfu/ml | | cfu/ml | log cfu/ml | |
| 0 | 1.04E+06 | 6.02 | 6.02 | 1.58E+05 | 5.20 | 5.20 | 1.98E+06 | 6.30 | 6.30 |
| 2 | 5.60E+05 | 5.75 | 5.75 | 8.60E+05 | 5.93 | 5.93 | 9.00E+05 | 5.95 | 5.95 |
| 4 | 5.00E+05 | 5.70 | 5.70 | 6.00E+05 | 5.78 | 5.78 | 1.12E+05 | 5.05 | 5.05 |
| 6 | 8.60E+05 | 5.93 | 5.93 | 5.40E+05 | 5.73 | 5.73 | 9.80E+05 | 5.99 | 5.99 |
| 24 | 1.04E+06 | 6.02 | 6.02 | 7.60E+05 | 5.88 | 5.88 | 8.00E+05 | 5.90 | 5.90 |

TABLE 3-continued

| | Trials with 300 μg/ml DPOLC | | | | | | | | |
|---|---|---|---|---|---|---|---|---|---|
| | E. coli DPOLC | | | P. aeruginosa DPOLC | | | S. aureus DPOLC | | |
| Time (h) | cfu/ml | log cfu/ml | | cfu/ml | log cfu/ml | | cfu/ml | log cfu/ml | |
| 0 | 4.60E+05 | 5.66 | 5.66 | 1.04E+06 | 6.02 | 6.02 | 1.22E+05 | 5.09 | 5.09 |
| 2 | <20 | <1.30 | 1.30 | <20 | <1.30 | 1.30 | 2.20E+02 | 2.34 | 2.34 |
| 4 | <20 | <1.30 | 1.30 | <20 | <1.30 | 1.30 | <20 | <1.30 | 1.30 |
| 6 | <20 | <1.30 | 1.30 | <20 | <1.30 | 1.30 | <20 | <1.30 | 1.30 |
| 24 | <20 | <1.30 | 1.30 | <20 | <1.30 | 1.30 | <20 | <1.30 | 1.30 |

What is claimed is:

1. An aqueous solution comprising a reactive chlorine compound selected from the group consisting of

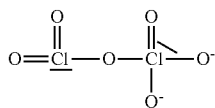

(I)

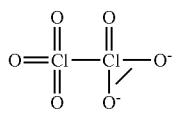

(II)

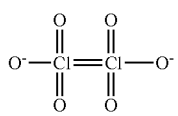

(III)

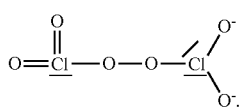

(IV)

salts thereof, and mixtures thereof.

2. The aqueous solution according to claim 1, wherein the total concentration of reactive chlorine compound is at least 0.01 M.

3. The aqueous solution according to claim 1, wherein the total concentration of reactive chlorine compound is about 0.05 M to about 1 M.

4. The aqueous solution according to claim 1, wherein the total concentration of reactive chlorine compound is about 1 mM to about 5 mM.

5. The aqueous solution according to claim 1, wherein the total concentration of reactive chlorine compound is about 0.5 mM to about 5 mM.

6. The aqueous solution according to claim 1, comprising a compound having a peak at about 189 m/z in a mass spectrum.

7. The aqueous solution according to claim 6, wherein the peak at about 189 m/z in the mass spectrum has a higher intensity than a peak at about 99 m/z in the mass spectrum.

8. The aqueous solution according to claim 1, comprising a compound having a peak at about 83.2 m/z in a mass spectrum.

9. The aqueous solution according to claim 8, wherein the peak at about 83.2 m/z in the mass spectrum has a higher intensity than a peak at about 99 m/z in the mass spectrum.

10. The aqueous solution according to claim 1, comprising a compound having a retention time of about 19.77 minutes by ion chromatography, wherein under the same ion chromatography conditions, the reference substance NaCl has a retention time of about 13.21 minutes and the reference substance NaClO$_3$ has a retention time of about 16.26 minutes.

11. The aqueous solution according to claim 10, wherein a peak having a retention time of about 16.26 minutes is not detected by ion chromatography.

12. The aqueous solution according to claim 10, wherein a peak having a retention time of about 15 minutes is detected by ion chromatography.

13. The aqueous solution of claim 1, further comprising an additional reactive chlorine compound selected from the group consisting of peroxochlorous acid of formula O=ClOOH, an anion of peroxochlorous acid of formula O=ClOO$^-$, salts thereof, and mixtures thereof.

14. A pharmaceutical composition for treatment of wounds or enhancement of tissue regeneration comprising an effective dosage of an aqueous solution according to claim 1.

15. The pharmaceutical composition according to claim 14 formulated for parenteral or topical administration.

* * * * *